(12) United States Patent  (10) Patent No.: US 7,160,320 B2
Duran  (45) Date of Patent: Jan. 9, 2007

(54) REED VALVE FOR IMPLANTATION INTO MAMMALIAN BLOOD VESSELS AND HEART WITH OPTIONAL TEMPORARY OR PERMANENT SUPPORT

(75) Inventor: Carlos Duran, Missoula, MT (US)

(73) Assignee: The International Heart Institute of Montana Foundation, Missoula, MT (US)

( * ) Notice: Subject to any disclaimer, the term of this patent is extended or adjusted under 35 U.S.C. 154(b) by 265 days.

(21) Appl. No.: 10/412,377

(22) Filed: Apr. 11, 2003

(65) Prior Publication Data

US 2005/0055079 A1    Mar. 10, 2005

Related U.S. Application Data

(60) Provisional application No. 60/373,171, filed on Apr. 16, 2002.

(51) Int. Cl.
A61F 2/06  (2006.01)
A61F 2/24  (2006.01)
A61B 19/00  (2006.01)

(52) U.S. Cl. ............ 623/1.24; 623/2.12; 128/898
(58) Field of Classification Search ............ 623/1.1, 623/1.11, 1.13, 1.23–1.26, 1.32–1.36, 902–903, 623/909, 916, 921, 925, 2.1, 2.12–2.19, 2.33–2.42; 128/898; 600/36
See application file for complete search history.

(56) References Cited

U.S. PATENT DOCUMENTS

| 5,156,621 | A | 10/1992 | Navia et al. |
| 5,197,979 | A | 3/1993 | Quintero et al. |
| 5,480,424 | A | 1/1996 | Cox |
| 5,713,950 | A | 2/1998 | Cox |
| 5,728,153 | A | 3/1998 | Menkis et al. |
| 5,824,036 | A | 10/1998 | Lauterjung |
| 5,885,228 | A | 3/1999 | Rosenman et al. |
| 6,092,529 | A | 7/2000 | Cox |
| 6,270,526 | B1 | 8/2001 | Cox |
| 6,277,555 | B1 | 8/2001 | Duran et al. |
| 6,312,464 | B1 | 11/2001 | Navia |

(Continued)

FOREIGN PATENT DOCUMENTS

WO   WO 200204037 A1 * 1/2002

OTHER PUBLICATIONS

Duran et al. A Method for Placing a Total Aortic Homograft into the Subcoronary Position. *Lancet*. 1962; 2: 488-489.

(Continued)

*Primary Examiner*—David J. Isabella
(74) *Attorney, Agent, or Firm*—Gabor L. Szekeres (57) ABSTRACT

A multi-leaflet valve adapted to serve as a prosthesis for diseased native valve of a mammal is constructed of biologic membrane or of biocompatible synthetic membrane. The valve has the shape of a truncated cone that has an inflow and an outflow orifice with leaflets forming the outflow orifice and forming a plurality of commissures. A first flexible stent is removably affixed in a substantially circular fashion around the truncated cone in proximity of the inflow orifice, and a second flexible stent is removably affixed at the location of the commissures to form a circle around the truncated cone in proximity of the outflow orifice. The stents maintain the shape of the valve during the surgical implantation procedure. Each stent independently can be left in the valve or can be removed during the implantation procedure based upon the judgement of the cardiac surgeon performing the implantation procedure. A holder designed to maintain the geometry of the valve during implantation to a mammal is also disclosed.

4 Claims, 5 Drawing Sheets

U.S. PATENT DOCUMENTS 6,352,708 B1    3/2002   Duran et al.
6,491,511 B1   12/2002   Duran et al.
6,682,559 B1 *  1/2004   Myers et al. .............. 623/2.13

OTHER PUBLICATIONS

Barret-Boyes et al. Long-term Follow-up on Patients with the Antibiotic Sterilized Aortic Homograft Valve Inserted Free Hand in the Aortic Position. *Circulation*. 1987; 75: 768-772.

Binet et al. Heterologous Aortic Valve Transplantation. *Lancet*. 1965; 2: 1275-1277.

David et al. Aortic Valve Replacement with Stentless Porcine Aortic Valve Bioprosthesis. *J. Thorac Cardiovasc Surg*. 1990; 99: 113-118.

Duran et al. A Prosthetic Heart Valve Holder. *Lancet*. 1965; 3: 22-23.

O'Brien MF. The Cryolife-O'Brien Composite Stentless Aortic Porcine Zenograft Valve: Follow up of 135 Patients>In Piwnicaa A, Wetaby S eds. Surgery for Acquired Aortic Valve Disease. *Oxford UK: Isis Medical Media Ltd*. 1997; 417-422.

Ross. Homograft Replacement of the Aortic Valve. *Lancet*. 1962; 2:487.

* cited by examiner

REED VALVE FOR IMPLANTATION INTO MAMMALIAN BLOOD VESSELS AND HEART WITH OPTIONAL TEMPORARY OR PERMANENT SUPPORT

CROSS-REFERENCE TO PRIORITY APPLICATION

The present application claims the priority of provisional application Ser. No. 60/373,171 filed on Apr. 16, 2002.

BACKGROUND OF THE INVENTION

1. Field of the Invention

The present invention is in the field of one-way valves designed to replace diseased venous or arterial valves present in the circulatory system. More specifically, the present invention is directed to the replacement of the aortic, pulmonary, or peripheral vein valves. The present invention is also directed to a holder that maintains the valve's geometry during its surgical implantation and assists the surgeon to orient it correctly.

2. Description of Background Art

The Sigmoid Valves

The mammalian circulation needs the presence of one-way valves to maintain forward blood flow. These valves are found in the outflow of the right and left ventricles ("pulmonary" and "aortic" valves, respectively) and in the large veins. Because of their similar anatomic structure, they are called "sigmoid" or "semilunar" valves. This common structure consists of one, two, or three very thin flaps called "cusps" or "leaflets." Each flap has a semicircular shape with a curved free edge and a curved base that is inserted into the vessel wall. The insertion of the free edge of the cusp to the vessel wall is called the "commissure." Immediately downstream to each leaflet, the wall of the vessel has a dilatation or bulge called the "sinus of Valsalva." There are as many sinuses of Valsalva as leaflets; a trileaflet valve has three sinuses. Historically, the sigmoid valves were understood to be formed only by these leaflets. Recent studies by the present inventor and colleagues have shown however that the aortic valve (as a model of all sigmoid valves) must include two or three leaflets; their crown-shaped base of attachment to the vessel wall known to cardiac surgeons as the "valve annulus;" the sinuses of Valsalva, the sinotubular junction or supra-aortic crests that delineate the upper limit of each sinus of Valsalva, and in the case of the aortic valve, the origin of the two coronary arteries or "coronary ostia."

The nature of dynamic changes that occur in the geometry of the aortic and pulmonary valves during the cardiac cycle was also studied recently by the present inventor and colleagues using ultrasound crystals to provide data. Three-dimensional reconstructions were obtained at 200 frames per second. These newly acquired anatomic and physiologic data have a very significant impact on the design of new sigmoid prostheses and constitute the scientific basis for the present invention.

Sigmoid Valve Replacement

In disease, the function of the sigmoid valves is impaired either through narrowing of the valve ("stenosis") or lack of complete closure, which results in backflow ("regurgitation"). In both circumstances, the whole circulation of the blood and of the heart is altered giving rise to severe symptoms in the patient.

Cardiac sigmoid valve replacement with prosthesis is a tribute to the imagination of cardiac surgeons and engineers. After open-heart surgery became available, parallel development of mechanical and tissue valves continued. Further description here concentrates only on tissue valves, because only these are truly relevant as background to the present invention. In the decade of the 1960s, there was an explosion of new tissue valves. At Oxford University, England, a surgical method was developed to dissect, prepare, and implant a human cadaver aortic valve in its anatomic (i.e., subcoronary) position (see Duran et al.: A method for placing a total aortic homograft into the subcoronary position. *Lancet* 1962;2:488–489). This technique was applied for the first time in 1962 (see Ross: Homograft replacement of the aortic valve. *Lancet* 1962;2:487). It consisted of removing as much non-valvular tissue as possible so that only the three leaflets were sutured to the patient. This was the origin of the use of homografts that even today remain the preferred valve replacement alternative because the patient does not need permanent anticoagulation therapy. This operation was improved by Barrat-Boyes, who placed the aortic homograft with a double suture line (see Barrat-Boyes et al.: Long-term follow-up on patients with the antibiotic sterilized aortic homograft valve inserted free hand in the aortic position. *Circulation* 1987;75:768–772). The homograft was dissected in a more tubular fashion, and was held in position by a proximal suture line that anchored the inflow orifice of the homograft to the outflow of the ventricle and a distal suture line that joined the homograft aortic wall to the aortic wall of the patient. This technique has become the preferred method for the surgical implantation of all aortic homografts and stentless bioprostheses.

Because of the difficulty of obtaining cadaver valves, the art also developed an interest in using porcine valves. In 1965, the first aortic xenograft (porcine) clinical implant was performed (see Binet et al.: Heterologous Aortic Valve Transplantation. *Lancet* 1965;2:1275–1277). The technical difficulty of correctly implanting these stentless valves gave rise to the idea of mounting the porcine valves into a frame or stent made of metal or plastic covered with DACRON™ cloth. These stented xenogeneic valves are called "bioprostheses," and presently constitute approximately 40% of all heart valve replacements.

More recently, awareness of the limitations of the mounted, stented bioprostheses has rekindled the interest in the "stentless bioprosthesis," where chemically treated porcine aortic valves are supplied as a complete aortic root that can be used as a complete root replacement or can be cut down to fit within the aortic root of the patient using the Barrat-Boyes technique (see David et al.: Aortic Valve Replacement with Stentless Porcine Aortic Valve Bioprosthesis. *J Thorac Cardiovasc Surg* 1990;99:113–118). The surgical techniques of implanting such stentless valves are far more demanding than when a standard stented valve is used. The main technical difficulties are due to the floppiness of the valve, resulting in a defective implantation, and in the case of the aortic valve, interference with the coronary ostia. These difficulties have significantly limited the use of stentless valves.

A different surgical alternative is valve repair. Because of the long-standing interest in mitral valve repair, the art tried to expand the field of repair to the aortic valve. It soon became apparent that the main problem, different from the mitral valve, was the lack of sufficient valve tissue to achieve competence. As a solution, the pericardium of the patient was selected to extend the aortic leaflets. In this technique, the pericardium is fixed and trimmed using specially designed molds (see U.S. Pat. Nos. 6,352,708 and 6,491, 511). Sixty-five patients underwent this procedure and are being followed for a maximum of 12 years with satisfactory results. In the course of developing the present invention, a series of in vitro and in vivo experiments were conducted. These experiments led to the present invention, which renders the surgical implantation technique of using pericardium or like membrane in valve replacement significantly less difficult.

SUMMARY OF THE INVENTION

In its overall aspect, the present invention is a novel system designed to provide a sigmoid tissue valve with stents that simplify its implantation and that can be left in place permanently or removed if a stentless valve is preferred according to the judgment of the surgeon. The present invention is to be used for the replacement of the diseased aortic, pulmonary, or great vein valves. It comprises the following basic elements: a sigmoid valve constructed of biologic membrane or of biocompatible synthetic membrane; two supporting but removable frames or stents; and as an adjunct for facilitating the surgical technique of implantation, a holding device to support the valve during the implantation.

DETAILED DESCRIPTION OF THE INVENTION

The following specification, taken in conjunction with the drawings, sets forth the preferred embodiments of the present invention. The embodiments of the invention disclosed herein are the best modes contemplated by the inventor for carrying out his invention in a commercial environment, although it should be understood that various modifications can be accomplished within the parameters of the present invention.

General Description

The valve

The bicuspid or tricuspid valve of the invention (see for example FIG. 6) can be made of a flexible, flat membrane of biocompatible synthetic or biologic material of autologous, homologous, or heterologous tissue, such as pericardium, pleura, peritoneum, or dura mater. The membrane is placed on a template of the appropriate size and shape (see FIGS. 3 and 4). The material is trimmed to acquire a trapezoidal shape of the desired form. The trimmed membrane has such a shape that when its lateral aspects are joined together (see FIG. 6), a truncated cone is formed with a base (or inflow) orifice slightly larger than its distal (or outflow) orifice. The inflow orifice is cut into a single plane and the outflow orifice is trimmed into two or three curvatures corresponding to the three free edges of the new bi-leaflet or tri-leaflet prosthesis. The points where the free edge curvatures are in continuity correspond to the two or three commissures of the new prosthesis. The height of the membrane at the level of the three commissures corresponds to the distance between the base of a normal sigmoid valve and its commissures, adding a few millimeters to increase the area of coaptation of the new leaflets.

Alternatively, the valve of the invention can be made of an already existing conduit of synthetic or biologic origin such as artery, vein, or gut of autologous, homologous, or heterologous origin. A conduit of the desired length and diameter is selected. Its length must correspond to the calculated distance between the base and the top of the commissures of the natural sigmoid valve adding a few millimeters to ensure good leaflet coaptation. One extremity of the conduit is sectioned perpendicular to the direction of the conduit. This end will constitute the inflow orifice. The other end of the conduit or outflow orifice of the prosthesis is trimmed according to whether a bi-leaflet or tri-leaflet valve is constructed. The membrane is trimmed so that two or three equidistant curvatures result corresponding to the free edges of the two or three new leaflets. The point where the curvatures meet corresponds to the valve commissures.

As still another alternative, the valve of the invention is constructed of a natural, biologic sigmoid valve, such as the pulmonary, aortic, or vein roots of autologous, homologous, or heterologous origin. The natural root is dissected so that a minimum of non-leaflet tissue is left. The inflow orifice is then formed by a narrow horizontal band of cardiac muscle, fibrous tissue, or vessel according to the origin of the tissue. The outflow orifice has a scalloped shape that follows the contours of the insertion of the leaflets, leaving a few millimeters of the vessel wall. This manner of preparing a valve by dissection is described by Duran et al.: *Lancet* 1962;2:488–489, and is well known in the art. The Duran et al.: *Lancet* 1962;2:488–489 publication is expressly incorporated herein by reference. One of the novel features of the present invention is the presence of separate circular stents placed in the inflow and outflow orifices and the manner of suturing of the outflow orifice. These features are described in detail below.

Surgical insertion of the prosthesis of the present invention starts by suturing its inflow orifice to the annulus of the patient's sigmoid valve with running or interrupted sutures along a horizontal line, which is well known in the previous art. The basal supporting stent must be included in this suture. After this suture is finished, if the surgeon desires a completely stentless valve, the inflow stent is cut and removed. The distal anchoring of the prosthesis is limited to suturing the commissures to the patient's vessel wall a few millimeters above the native commissures. The outflow stent must be incorporated in these sutures. The outflow stent can be cut and removed or left in place. If left in place, the portions of the outflow stent between the commissural sutures must be secured to the patient's vessel wall with a simple running suture along the sinotubular ridge or junction.

The Stents

In accordance with the present invention, both the base of the valve (sometimes termed "reed valve") that forms the inflow orifice and also the distal (or outflow) orifice are held with a separate circular stent so that the inflow and outflow orifices of the new prosthesis maintain their circular shape during insertion. The flexible stents incorporated in the valve of the invention can be made of thin metal wire or thin plastic ring attached by sutures to the inflow and outflow orifices of the prosthesis. The stents can also be formed by suturing thick polypropylene or other suitable plastic filament in a circular fashion around the inflow and outflow orifices of the valve. After removal of the patient's diseased valve, the base of the prosthesis valve is sutured to the patient's valve annulus with interrupted or running sutures, a surgical technique well known in the previous art. If the surgeon desires to avoid any stent, the basal stent is cut and pulled from the prosthesis. Next, the commissural points of the truncated cone corresponding to the outflow orifice of the prosthesis are sutured with pledgeted sutures to the patient's vessel wall, approximately 2 to 3 mm beyond the patient's own commissures. If the surgeon decides to have a completely stentless prosthesis, the upper (or outflow) stent is cut and removed. If the surgeon decides to retain the outflow stent, a running suture with standard small-caliber filament is used to anchor the stent to the patient's vessel wall at the level of the sinotubular junction. Whereas the inflow stent is designed to maintain the circular geometry of the inflow orifice of the prosthesis, the outflow stent is designed to maintain equal distances between the two or three commissures of the prosthesis during implantation. This is particularly important in cases where the distance between the patient's commissures is variable. In these cases, the outflow stent will indicate where to suture the commissures of the prosthesis to the patient's vessel wall. The decision to retain the two supporting stents depends on the pathology encountered by the surgeon. In some patients, the base of the sigmoid valve is abnormally dilated; in others, the sinotubular junction is abnormally dilated; and in others, both base and sinotubular junctions are dilated. These cases require continued presence of the support offered by the inflow and outflow stents to avoid progressive dilatation at these levels.

Figure 14A:
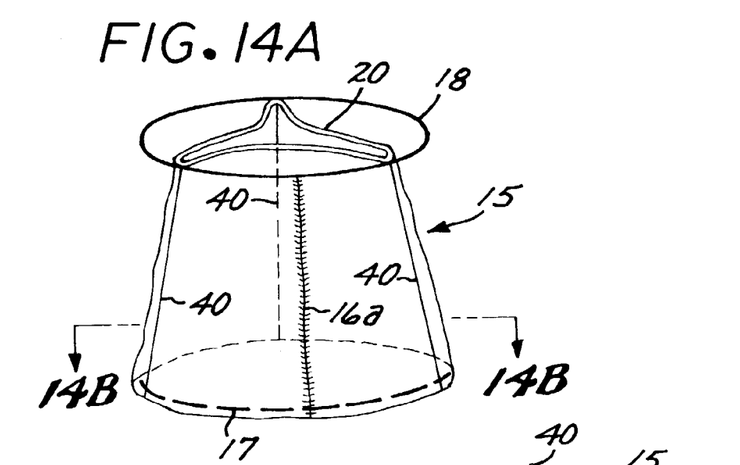
FIG. 14A is a schematic view of still another preferred embodiment of the valve of the present invention.
Figure 14B:
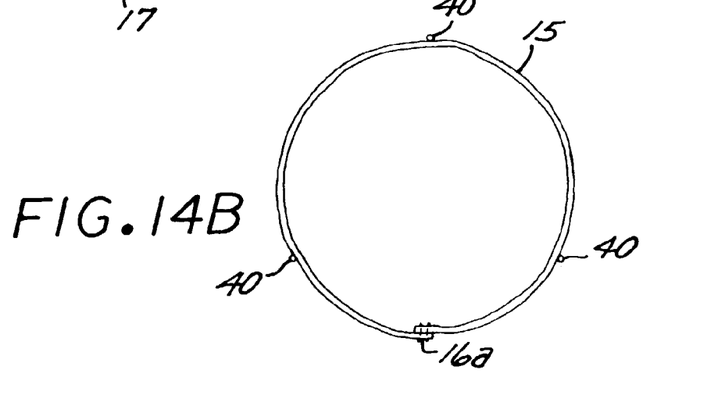
FIG. 14B is a cross-sectional view taken on lines 14B,14B of FIG. 14A.

In another embodiment of the invention (shown in FIG. 14), the two circular inflow and outflow removable stents are connected with three vertical arms made of a thin wire or flexible plastic material. These connectors join the inflow and outflow stents at the level corresponding to the commissures of the tissue valve. A variety of techniques well known in the art can be used to join these connectors to the inflow and outflow stents. The connectors can also be cut and removed after the reed valve has been sutured into the patient. The object of the connectors is to facilitate the correct orientation and distance between the inflow and outflow orifices of the tissue valve after the inflow orifice has been sutured in place. Twisting and over- or under-stretching of the valve is therefore avoided.

The Valve Holder

A holder (see FIGS. 10A, 10B, 10C, 11, 12A, 12B, and 12C) is provided to support the new sigmoid tissue valve solely before and during its surgical implantation. The surgical holder consists of two circular rings or disks of the appropriate diameter connected by a rod that allows the operator to change the distance between the two rings or disks. The sigmoid valve can be attached to the rings or disks with simple fasteners, such as sutures. When the holder includes disks then each disk has a circumferential groove to secure the inflow and outflow orifices of the sigmoid valve with fasteners such as a circumferential suture or an elastic band. The rings or disks have three markers at 120 degrees apart. The holder is made of suitable plastic or metal alloy known in the art. The second or outflow disk or ring can be moved along the rod to any point, from close to the inflow disk or ring to a predetermined distance from the inflow disk or ring, according to the size of the reed valve. Therefore, the distance between the rings or disks can be varied within a pre-established range. Also, although the minimal distance between inflow and outflow orifices is limited by contact between the two disks or rings, as applicable, the maximum distance is limited by a stopper or other means provided in the connecting rod. For example, the rod supporting the two disks instead of having a circular section, has a triangular section only between the maximum desired distance between disks (FIGS. 10B and 10C). The cross-section of the rod beyond the outflow disk has a circular section (FIG. 10B). Therefore, the maximum distance between disks is limited by the length of the triangular section of the rod.

The second embodiment of the holder of the present invention shown in FIGS. 10B and 10C also includes three substantially equal chords that connect the inflow and outflow disks. These chords are located at the level of the commissures of the reed valve, and their length corresponds to the total height of the reed valve. The purpose of these two techniques (stopper or cords) for limiting the maximum distance between the disks (and therefore between the inflow and outflow orifices of the reed valve) is to achieve correct deployment of the reed valve without either folding it if the inflow and outflow orifices are too close or unduly stretching the tissue if the inflow and outflow orifices of the reed valve are too far apart.

Figure 12A:
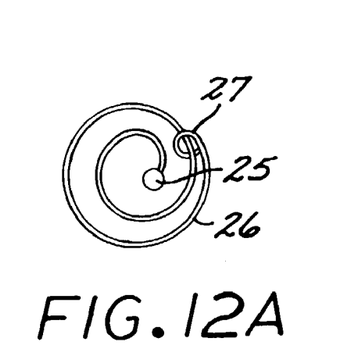
FIGS. 12A and 12C are schematic views illustrating the adaptation of the rings of the first preferred embodiment of the holder for insertion and withdrawal from the valve of the invention.
Figure 12B:
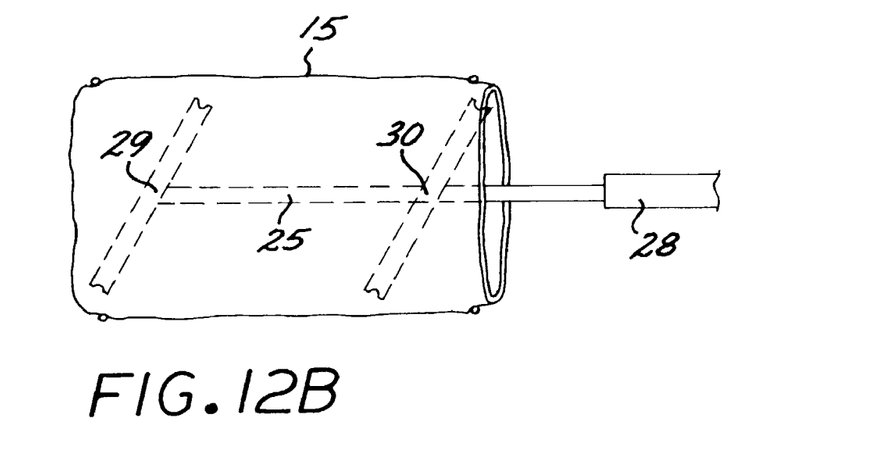
FIG. 12B is a schematic view illustrating the adaptation of the disks of the second preferred embodiment of the holder for insertion and withdrawal from the valve of the invention.

When the holder of the invention is used to support the valve by placing the holder inside the valve, then a mechanism or means need to be provided to temporarily reduce the effective diameter of the holder so that it can be inserted into the valve, and be removed from it to complete the surgical implantation process. The first embodiment shown in FIGS. 10A and 12A and 12C accomplishes this by virtue of the rings being contractible and expandable, as described in more detail below. In the second preferred embodiment shown in FIGS. 10B and 12B the disks are capable of changing their angle in relation to the rod (FIG. 12B). In one position the disks are at 45 degrees to the rod and in a second position the disks are perpendicular to the rod. The holder is introduced through the valve with the disks at 45 degrees and once in the correct location the disks are moved to the perpendicular (and wider) position.

The holder of the present invention can be disposable. Therefore, it is contemplated that a set of different size holders of the disposable kind are provided with different disk diameters and maximum distance between disks appropriate to the corresponding set of reed valve diameters. The contemplated diameters of holders and tissue valves of the present invention vary between 17 mm and 31 mm in steps of 2 mm. In one aspect of the invention, pre-manufactured valves are made available to surgeons already mounted (as described below) on appropriate sized holders.

Another preferred embodiment (not shown in the drawing figures) of the holder of the present invention is a multiple-use holder that is preferably made of metal. The disks of the holder are split into several equal segments that can expand from a minimum diameter of about 17 mm (when all segments of the disk are in contact) to a maximum of 30 mm when separated.

Figure 13:
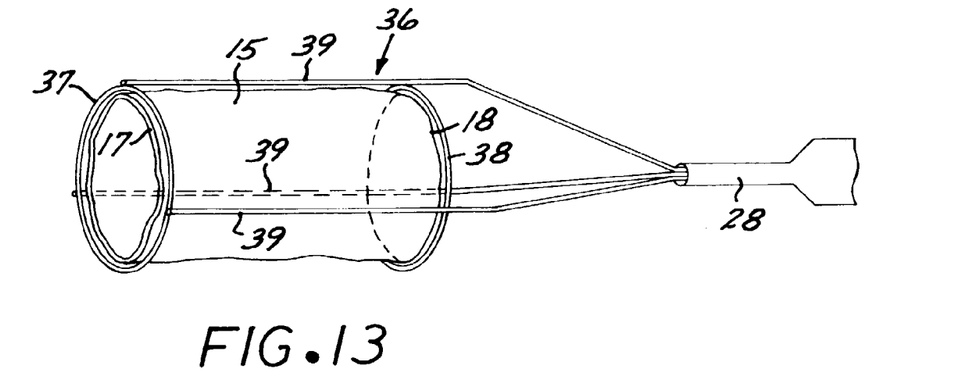
FIG. 13 is a schematic representation of still another preferred embodiment of valve holder.

Whereas the above embodiments contemplate a holder placed within the valve, another alternative is to place the holder outside the valve (as shown in FIG. 13). The holder has a general design of a cage with the valve held within it. The cage consists of two rings to which the inflow and outflow orifices of the valve are anchored. The disks are connected with three vertical rods which are joined together beyond the outflow ring and continued as a single rod that terminates in a handle that holds the cage and valve during its surgical implantation. The valve and its stents are held to the holder with glue, pins, sutures or other fastening methods well known in the art.

During surgery, the sigmoid valve is supported by the holder while the proximal anastomosis is performed. The sutures that have been passed through the patient's valve annulus are passed through the inflow orifice of the sigmoid valve while still held by the holder. After these sutures have been passed, the two disks of the holder are brought together so that the surgeon can tie the sutures. After the proximal anastomosis is completed, the distal disk is separated as far as possible from the proximal disk that holds the outflow orifice of the sigmoid valve. After the outflow sutures have been placed, the entire holder is removed in a manner described below.

Test Results

The prosthesis or reed valve of the present invention has been tested both in vitro and in vivo in our laboratories. Specifically, prototypes were tested in a "pulse duplicator" or mock circulation rig showing that such a simple valve mechanism functioned perfectly well. Further work showed that temporary support of the inflow and outflow orifices of the valve significantly simplified its surgical implantation. Models of such a device were implanted in the aortic position of isolated pig hearts and tested in a mock circulation rig. The function of the valve in terms of transvalvular gradients and competence was excellent. These experiments were followed with in vivo testing.

The reed valve of the present invention was implanted in six adult sheep, under cardiopulmonary bypass in the sub-coronary position of the aortic valve. The pericardium of the sheep was excised, treated with 0.5% buffered glutaraldehyde, and trimmed in a trapezoid shape. A 2/0 polypropylene suture was threaded through the base of the trapezoid to serve as a stent for the inflow orifice. The lateral aspects of the pericardium were sutured together, and the 2/0 suture was tied to form a truncated cone with the stented flexible circular base. After the proximal anastomosis (tying of the inflow orifice of the valve to the animal's native annulus) between the inflow orifice of the new valve and the left ventricular outflow tract (including the thick suture) was finished, the thick suture forming the inflow stent was cut and removed. The outflow orifice of the valve was secured at three equidistant points corresponding to the commissures. The prosthesis mean size was 19.7 mm, and the manufacturing time averaged 16 minutes. Cardiopulmonary bypass and ischemic mean times were 142.5 minutes and 100.2 minutes, respectively. The sheep were euthanized at 3, 7, and 27 days, and 5 months postoperatively. In all cases, the valve was competent and the single commissural stitches were well healed and anchored.

Detailed Explanation of how the Invention Differs from Prior Art

As far as the inventor is aware, there is no prosthesis similar to the reed valve of the present invention. Mechanical prostheses or valves have no similarity or relevance to the present invention. Among the standard bioprostheses, the Hancock-Medtronic porcine and the Carpentier-Edwards porcine and bovine are the most popular. These have a stent made of a polymer or alloy as a backbone with either a sinusoidal or circular shape with three vertical prongs covered with DACRON™. The tissue valve is sutured within the stent. Also, all stented prostheses, whether mechanical or biologic, have a so-called skirt consisting of a circular ring covered with DACRON™ cloth that is used to anchor the prosthesis to the patient's valve annulus with sutures.

Contrary to the stents of the above-noted "standard" bioprostheses, the present invention is different because it has two separate stents with completely different configuration than the standard stented valves. As noted, standard stented valves have a three-dimensional stent, which is contrary to the reed valve of the present invention that has two separate circular stents. Moreover, while the stents of the standard bioprostheses must remain in the patient, the stents of the present invention can be used to support the valve during its surgical implantation and then be removed if the surgeon so desires, converting the temporary stented valve into a permanent stentless valve.

The sigmoid valve of the present invention is also completely different from other stentless valves, such as the cadaver or porcine sigmoid valves, because these tissue valves do not have a stent, which makes their surgical implantation more difficult. Moreover, most of the prior art stentless valves require two complete suture lines: one horizontal at the inflow orifice and another scalloped at the outflow orifice. Placing this second suture is technically difficult because of the danger of interfering with the coronary ostia. The reed valve of the present invention only requires one complete suture at the level of the inflow orifice.

Nevertheless, there are two types of stentless valves that do not require the second or outflow suture. The O'Brien (*O'Brien M F. The Cryolife-O'Brien composite stentless aortci porcine xenograft valve: Follow up of 135 patients>In Piwnicaa A, Wetaby S eds. Surgery for acquired aortic valve disease. Oxford UK: Isis Medical Media Ltd.* 1997; 417–422) and the Duran autologous pericardium valve (U.S. Pat. No. 6,491,511 B1). In both cases these single suture bioprostheses do not have any stent.

A different approach in the art was the principle of completely suturing the base or inflow orifice of the prosthesis to the patient's aortic valve annulus (as in all tissue valves) but limiting the outflow orifice suture to only the tips of the commissures.

U.S. Pat. Nos. 5,480,424, 5,713,950, 5,824,036, 6,092,529, and 6,270,526 describe a tubular structure that can be used for the replacement of the mitral, tricuspid, aortic, and pulmonary valves. These reference patents suggest the possible addition of a permanent mitral circular annuloplasty ring to the inflow orifice and propose the alternative of anchoring the commissures with a single stitch at each of the three commissures. The principle of anchoring the outflow orifice of a stentless valve only at the commissures is also described in U.S. Pat. Nos. 5,156,621 and 6,312,464.

The reed valve of the present invention substantially differs from the bioprostheses of U.S. Pat. Nos. 5,480,424, 5,713,950, 5,824,036, 6,092,529, 6,270,526, 5,156,621 and 6,312,464 because these reference valves have stents of completely different designs than the stents of the reed valve of the present invention. The stents of some of these patents comprise a DACRON™ conduit with a sewing skirt placed higher than the inflow orifice. Others suggest the possibility of adding a permanent mitral annuloplasty circular ring attached to the inflow orifice of the valve. These single stents or annuloplasty rings remain permanently in the implanted valves. In contrast, the present invention comprises two stents that can be removed if so desired by the surgeon.

In relation to the valve holder designed to maintain the geometry of the prosthetic valve during storage and surgical implantation, there are several models known in the prior art. Holding systems designed to hold the stent of permanently stented valves are not relevant as background to the holder of the present invention, which basically is concerned with the problem of holding a stentless valve.

The publication by Duran et al. *A prosthetic heart valve holder. Lancet* 1965;3:22–23 describes a device to hold a stentless aortic valve homograft during its implantation. A long handle that can be fixed to the surgical table at an appropriate angle terminates in several prongs that, when expanded, hold an already dissected aortic valve. All the sutures are passed through the valve and held in the holder so that the surgeon can pass them in an orderly fashion through the patient's aortic annulus.

U.S. Pat. No. 5,197,979 describes a disposable and detachable stentless valve holder affixed to a suturable covering on the aortic segment of a heart valve via sutures that pass through holes in the holder. A disadvantage of this holder is that the tissue valve needs to be attached to the holder with numerous sutures. This consumes operative time to affix and remove. Moreover, this prior art holder does not provide space between the valve and holder for tying the sutures between the valve and the heart.

U.S. Pat. No. 5,728,153 describes a surgical device for holding a stentless valve during implantation. The device has a cylindrical body that is introduced through the valve. Radial marking lines separated at 120 degrees are designed to correspond with the valve commissures, and annular grooves in the cylinder allow holding the valve with two pressure-exerting fasteners.

At first consideration, the holder of the present invention has some similarity to the holder of U.S. Pat. No. 5,728,153; however, the holder of the present invention differs from these reference patents (with emphasis on U.S. Pat. No. 5,728,153) because the holder of the present invention does not consist of a single cylinder as in U.S. Pat. No. 5,728,153. Rather, it comprises two disks that separately hold the inflow and the outflow orifices of the reed valve of the present invention. Moreover, unlike the present holder, the holder of U.S. Pat. No. 5,728,153 cannot change the distance between the inflow and outflow orifices of the tissue valve because it is a single structure. This is an important distinction, because the reference holder only holds the tissue valve when passing the sutures through its proximal (or inflow) orifice and must be removed when tying these sutures because insufficient space is available for the surgeon's fingers between the patient's aortic wall and the cylindrical holder. The holder of the present invention allows reduction of the distance between the inflow and outflow disks until the two come in contact; this thereby allows the surgeon to tie the inflow sutures while the holder is still in place. Still further, suturing of the distal (or outflow) orifice of the tissue valve held by the reference holder must be done after the holder has already been removed after tying the knots of the proximal anastomosis. The holder of the present invention can remain in place when passing and tying the commissural sutures because the distal disk of the stent can be moved along the rod until it reaches its appropriate distance from the inflow disk.

Determining the appropriate distance between the proximal and distal anastomosis of the tissue valve is important for the correct function of the valve. None of the previously described holders help the surgeon at the time of performing the fixation of the distal orifice of the valve because, as noted above, these prior art holders must be removed after the sutures of the proximal or inflow orifice have been passed. In contrast, the distance between the inflow and outflow disks of the holder of the present invention can be changed. Therefore, after suturing of the inflow orifice of the tissue valve is completed, the outflow disk can be moved as far out as possible to ensure the correct anchoring of the distal orifice, thereby avoiding unintentional folding of the valve tissue.

The holders of the prior art have a constant diameter; therefore, a set of different holder sizes must be manufactured to accommodate the different valve sizes. Whereas this is the case with one embodiment of the holder of the present invention, the holder of the present invention can also be constructed so as to allow changes in its diameter.

One of the techniques used for achieving expansion of the disks of the holder of the present invention is similar to the method described in U.S. Pat. No. 5,885,228, in connection with a valve sizer; i.e., a device that determines the diameter of the valve orifice after a diseased heart valve has been removed. The present invention is different from U.S. Pat. No. 5,885,228 because it does not relate to a measuring device, but to a valve holder. Moreover, the reference device may expand of a single disc or like structure, this embodiment of the valve holder of the present invention expands two disks or like structures.

Description of the Specific Embodiments

Figure 1A:
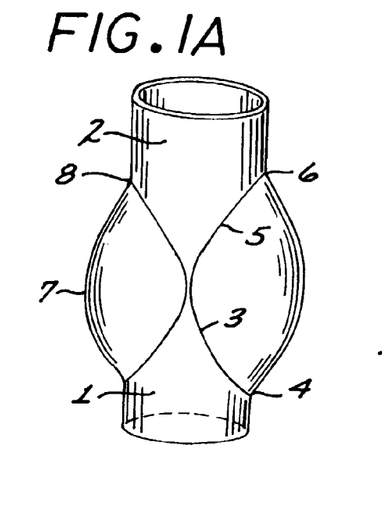
FIG. 1A is a schematic perspective view of a natural mammalian sigmoid valve root.
Figure 1B:
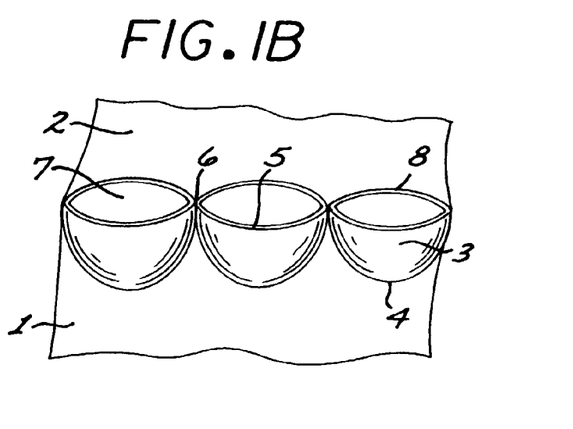
FIG. 1B is a schematic perspective view of the valve root of FIG. 1A that has been partially opened to show its natural components.

Referring now to the drawing figures, FIGS. 1A and 1B are sketches of the basic anatomic structure of a sigmoid valve, such as the aortic valve, pulmonary valve, or the valves present in peripheral veins. All of them are substantially a conduit or root with inflow 1 and outflow 2 orifices separated by three leaflets or cusps 3. FIG. 1A represents a longitudinal section of the root, and FIG. 1B a root that has been opened longitudinally to show its major components. The leaflets are attached to the valve annulus 4, which is scalloped as shown in FIG. 1B. The point where the free edges 5 of the leaflets or cusps 3 come in contact are the commissures 6. Opposite each leaflet, the vessel wall has three bulges or Sinuses of Valsalva 7. The distal (or outflow) limit of the sinuses of Valsalva 7 is the sinotubular junction 8.

Figure 2:
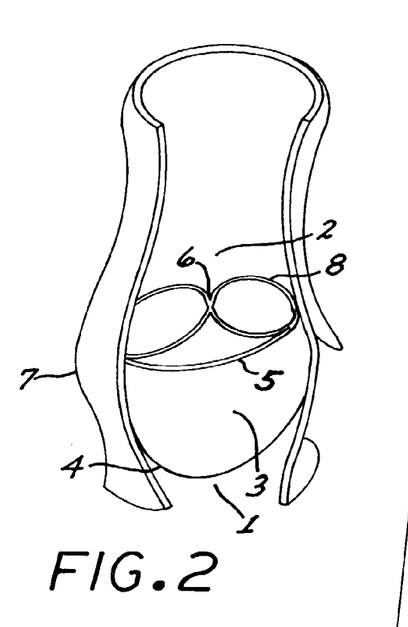
FIG. 2 is a schematic perspective view of a partially opened aortic root.

These structures are depicted closer to reality in FIG. 2, which represents an aortic valve root through an opened aorta. The anatomic landmarks, namely inflow orifice 1, outflow orifice 2, leaflets or cusps 3, base or annulus 4, free edge 5, commissures 6, sinuses of Valsalva 7, and sinotubular junction 8 are essential to be taken into consideration when manufacturing the valve prosthesis of the present invention.

Figure 3:
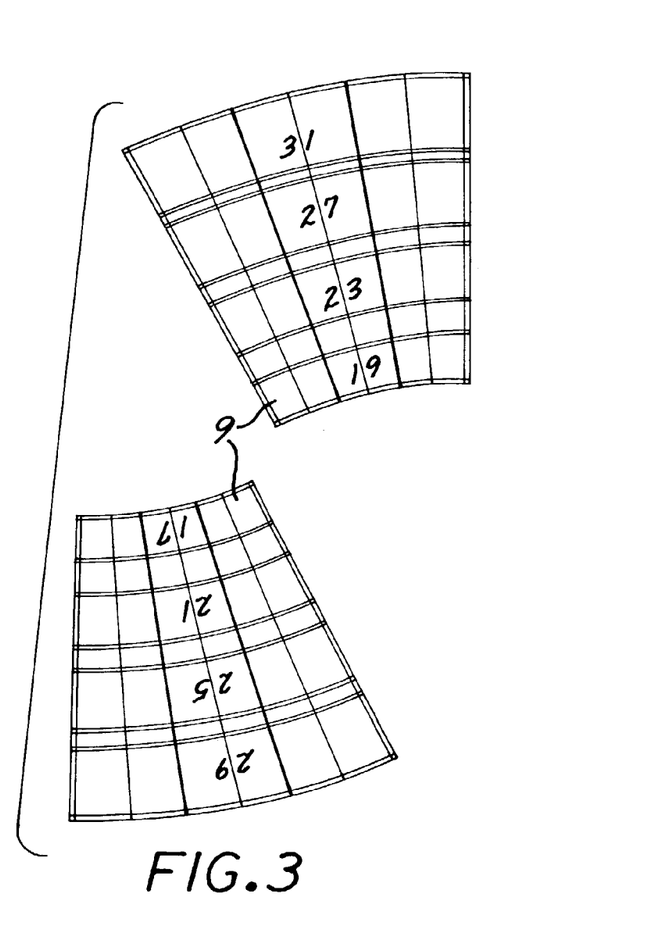
FIG. 3 is a top view of the preferred embodiments of templates that are used to construct the valve of the present invention.

The top view of FIG. 3 shows the dimensions of the flat templates 9 used for the construction of the reed valve of the present invention from a substantially flat, rectangular piece of biocompatible polymer or biologic membrane. Eight different sizes are represented in a 1:1 scale. The numbers correspond to the diameter of the inflow orifice of the valve after it is constructed. These templates can be made of rigid plastic (preferably translucent) or metal. After the diseased native valve has been completely removed, the diameter of the patient's valve annulus is measured with standard sizers well known in the art. The new reed valve is constructed according to this diameter. A template 9 of the corresponding size is selected. FIG. 3 shows the templates 9 for the construction of reed valves of the present invention with inflow diameters of 17, 21, 23, 25, 27, 29, and 31 mm. The number embossed in the template 9 indicates the size of valve prosthesis that will result from using that particular template.

Figure 4:
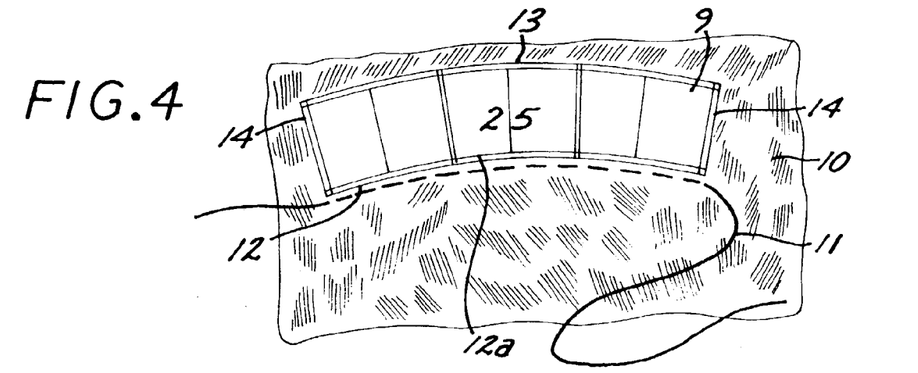
FIG. 4 is a top view showing the template placed on a flat biologic or synthetic membrane in the process of constructing the valve of the present invention.

FIG. 4 shows how the template 9 is used to trim the membrane to the appropriate size and shape. In this case, a 25 mm template 9 is used that corresponds to a valve with an inflow orifice diameter of 25 mm. The number "25" embossed in the template 9 indicates the diameter of the inflow orifice after the valve is constructed. A rectangular piece of biocompatible polymer or biologic membrane 10 is used for the manufacture of the reed valve of the present invention. In the preferred embodiment, a piece of pericardium of approximately 10×5 cm from the patient or from an animal such as pig, calf, or horse is obtained. The pericardium needs to be freed from alveolar tissue and treated according to whether it is autologous, homologous, or heterologous with chemical and physical treatments well known in the art (such as buffered glutaraldehyde). Alternatively, the pericardium can be treated with one of the treatments described in U.S. Pat. No. 6,352,708 or in U.S. Pat. No. 6,277,555 B1. The treated pericardium 10 is placed on a flat surface and covered with the template 9. In one of the preferred embodiments, a needle (not shown) carrying 2/0 polypropylene suture or wire 11 is then passed through the pericardium parallel and a few millimeters from the smaller curvature 12 of the template 9. This suture 11 will become the inflow stent of the prosthesis of the present invention. The pericardium is then trimmed with tools (not shown) such as scissors, surgical scalpel, or a cutting die following the shape of the template 9 but also including the stent suture 11. A trapezoidal piece of pericardium having a base 12*a*, a top 13, and two lateral sides 14 is then available for the construction of the reed valve 15.

Figure 5:
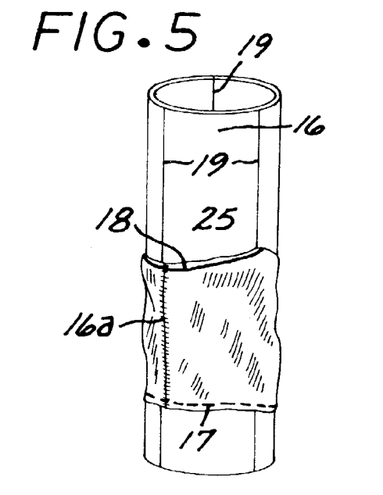
FIG. 5 is a perspective view showing another step in the process of constructing the valve of the present invention.

FIG. 5 demonstrates the steps to be followed for the construction of the reed valve 15 (see FIG. 6) with the trimmed flat piece of pericardium 10. The pericardium is wrapped around a mandrel 16 corresponding to the valve diameter (e.g., in this case with a diameter of 25 mm). The mandrel 16 can be a simple cylinder or, in the preferred embodiment, a truncated cone of slightly smaller dimensions than the intended valve. The two lateral sides 14 (shown in FIG. 4) of the pericardial trapezoid are then joined with a running suture of thin biocompatible filament 16*a*, such as 4/0 to 6/0 polypropylene. A truncated cone results with proximal (or inflow) and distal (or outflow) orifices. The previously placed thicker (2/0 polypropylene) suture 11 (shown in FIG. 4) is then tied over the truncated cone to form the flexible inflow stent 17. Another similar 2/0 suture is placed around the mandrel 16 and tied close to, but not through, the outflow orifice of the truncated cone. This suture forms the outflow flexible stent 18 of the reed valve 15. Three equidistant points, or commissures, of the truncated cone are selected. These points are sutured to three equidistant points of the outflow circular stent 18. The suture ends of the stents 17 and 18 can be joined with a surgical knot, if performed during surgery, or with methods such as crimping, glueing or other methods well known in the art. The mandrel 16 has three longitudinal marks 19 situated at 120 degrees apart to orient the placement of the commissural stitches in the outflow orifice of the reed valve 15. After the just described steps or operations are completed, the valve 15 is taken off the mandrel 16.

Figure 6:
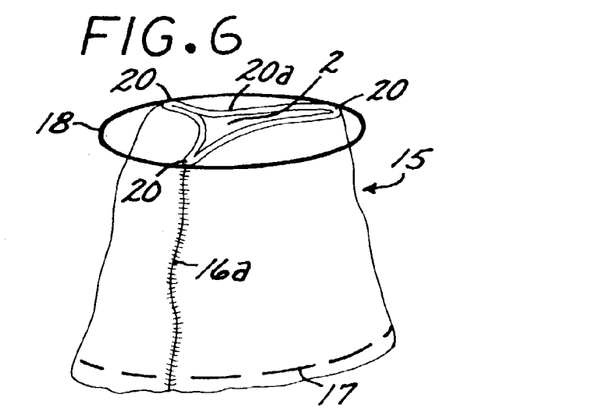
FIG. 6 is a perspective view of the valve of the present invention.

FIG. 6 is a perspective view of the final aspect of the reed valve 15 of the present invention. The pericardial truncated cone is formed by the suture 16*a* of the lateral sides of the formerly flat trapezoidal piece of pericardium 10. The inflow stent 17 holds the whole circumference of the valve inflow orifice 1. The outflow orifice 2 of the valve 15 is attached to the outflow stent 18 at only three equidistant points 20 separated by 120 degrees (marked 19 on the mandrel 16 in FIG. 5). While three commissures 20 are attached to the stent 18, the rest of the pericardial outflow orifice of the reed valve is free and forms the free edges 20*a* of the three leaflets 3.

Figure 7:
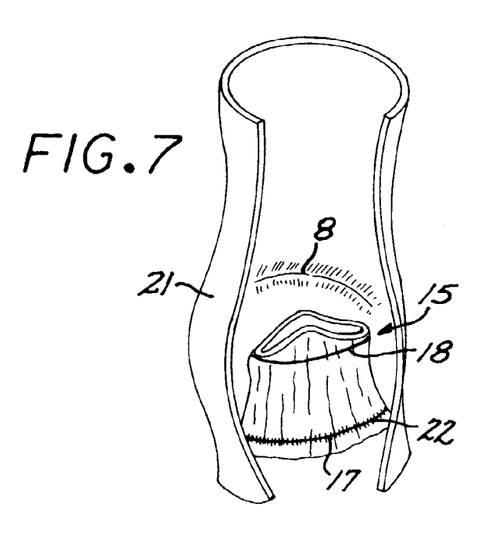
FIG. 7 is a schematic perspective view showing the valve of the present invention within the aortic root of a human patient.

FIG. 7 is a diagram showing the steps followed for the implantation of the reed valve 15 within the aortic root 21 of a patient. To complete the proximal anastomosis, the inflow orifice has been sutured to the patient's annulus with interrupted stitches 22 that include the inflow stent 17. If the surgeon (not shown) considers it appropriate to implant a stentless valve, the stent 17 is simply cut and removed. The distal (or outflow) orifice and stent 18 have not yet been sutured in place.

Figure 8:
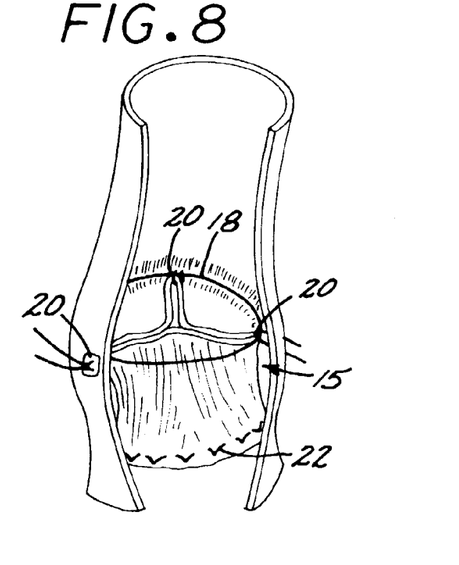
FIG. 8 is another schematic perspective view showing the valve of the present invention within the aortic root of a human patient. The inflow stent has been removed from the valve.

FIG. 8 is a perspective view of the partially implanted reed valve 15 of the present invention. The proximal (or inflow) anastomosis has been completed, and the stent 17 has been removed. The outflow orifice of the valve 15 has been attached at the three commissures 20. The outflow stent 18 is still only attached at the commissures 20. If the surgeon considers it appropriate to implant a stentless valve, the stent 18 is cut and removed.

Figure 9:
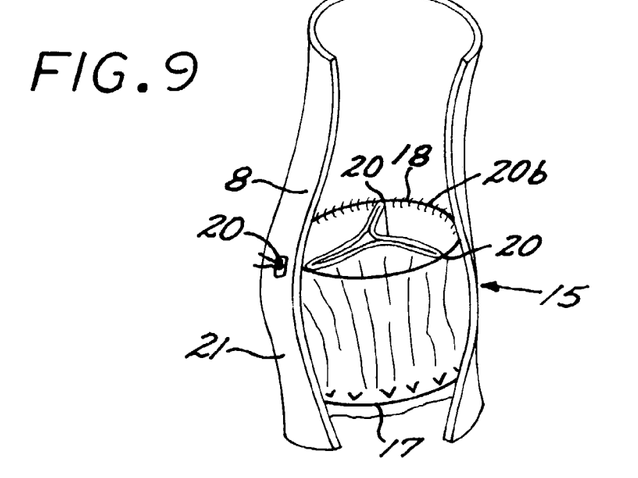
FIG. 9 is still another schematic perspective view showing the valve of the present invention within the aortic root of a human patient. Both the inflow and outflow stents are present in the valve.

FIG. 9 is a perspective view similar to FIG. 8. In the presence of a dilated annulus or sinotubular junction 8, both inflow 17 and outflow 18 stents can be left in place. In this case, the outflow stent 18 must be anchored to the patient's sinotubular junction 8 with a running suture 20*b*.

Figure 10A:
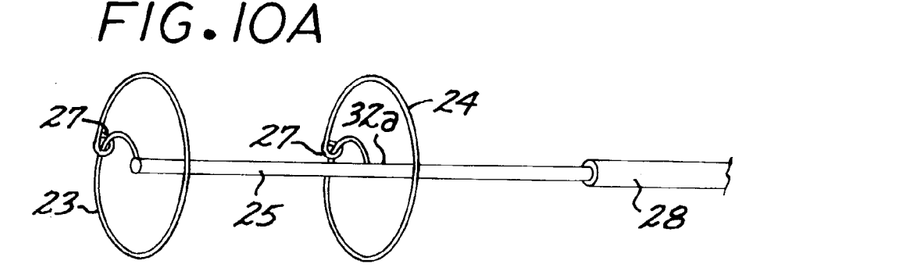
FIG. 10A is a perspective view of a preferred embodiment of the valve holder of the present invention.
Figures 10B, 10C:
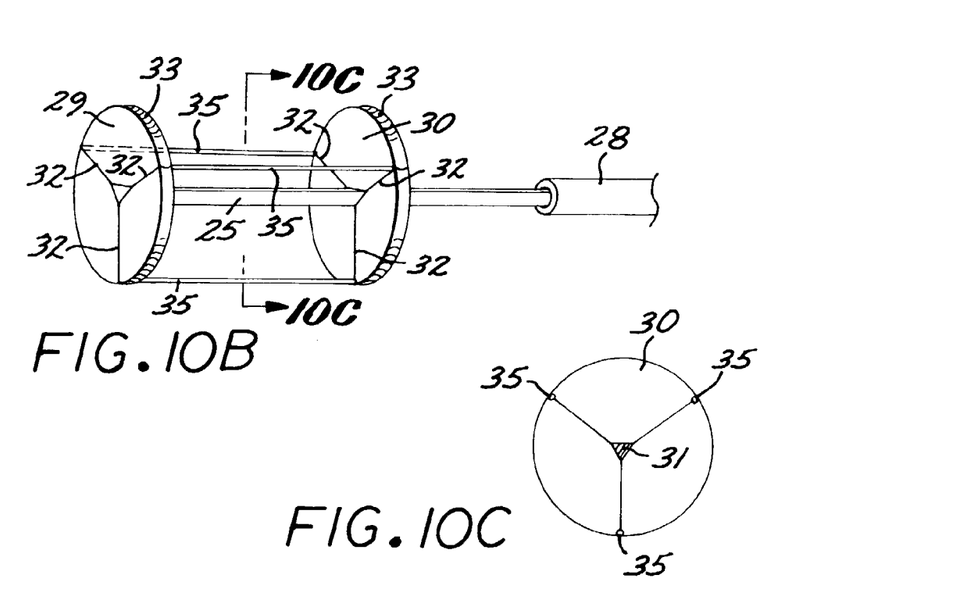
FIG. 10B is a perspective view of another preferred embodiment of the valve holder of the present invention.
FIG. 10C is a cross-sectional view taken on lines 10C,10C of FIG. 10B.
Figure 12C:
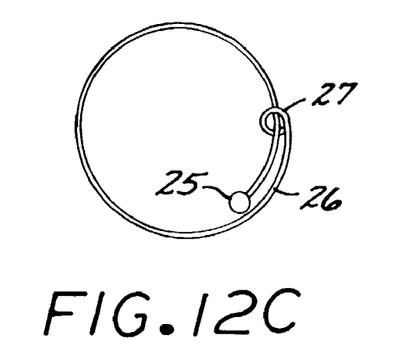

FIG. 10A is a perspective view of a first preferred embodiment of the holder of the present invention. Generally speaking the holder is designed to maintain the geometry of the reed valve 15 (shown in FIGS. 6 and 9) of the present invention before and during its implantation. One type of holder in accordance with the present invention is designed to be placed into the valve 15 of the invention, and to be removed therefrom when such removal becomes necessary during the surgical implantation process. The first preferred embodiment is such a holder. As is shown in FIGS. 10A, 12B and 12C two rings 23 and 24 made of suitable metal or plastic (preferably of metal) and having a maximum diameter slightly inferior to the valve are joined by a rod 25 that passes through the center of the rings 23 and 24. One extremity of the rod 25 is fixed to the inflow ring 23, but the outflow ring 24 can slide along the rod 25. In the first preferred embodiment the rod 25 has a circular cross-section along its entire length (as shown in FIG. 10A).

The rings 23 and 24 of the first embodiment are comprised of a wire spiral 26 (see FIG. 12A) that has one of the two ends of the wire attached to the rod 25 and the other ending in a loop 27 that encases the spiral 26. The rod 25 ends in a handle 28. Mechanical means or apparatus is included to enable turning of the handle 28 in one direction to roll the spiral 26 to decrease the diameter of both rings 23 and 24 and to turn the handle 28 in the other direction to increase the diameter of the rings 23 and 24. In this embodiment the variable diameter of the rings 23 and 24 renders it possible to place the holder into the valve 15 and to withdraw the holder from the valve 15 during the surgical process.

A second preferred embodiment of the holder of the invention is also the type that is placed inside the valve 15 to support it during surgery, and to be withdrawn from the valve 15 when this becomes appropriate during the surgical procedure. This preferred embodiment is shown in FIGS. 10B, 10C, 11 and 12B. Two disks 29 and 30 are mounted to the rod 25 and the rod 25 has a triangular cross-section 31 between the disks 29 and 30 for a distance corresponding to the height of the prosthesis. Each edge of the triangular cross-section 31 of the rod 25 corresponds with one the three markers 32 placed at 120 degrees on the surfaces of the disks 29 and 30, respectively. Beyond the maximum distance between the inflow 29 and outflow disk 30, the cross-section of the rod 25 is circular. The maximum distance between the disks 29 and 30 is determined by the maximum height of the valve 15 with which the holder is intended to be used.

The reason for providing a part of the rod 25 with the triangular cross-section 31 in the second preferred embodiment is as follows. First, it helps the surgeon (not shown) to determine where to affix the outflow orifice of the reed valve 15 to the patient's aortic wall. Proper function of the reed valve 15 must avoid expansion and overstretching of the pericardium. Second, it avoids twisting the reed valve 15 so that the inflow and outflow orifices are not properly aligned. The triangular cross-section 31 of the rod 25 ensures correct alignment of the commissures 20 of the outflow orifice of the prosthesis 15. In the first preferred embodiment of the holder this function is served by a stop 32*a* at the end of the rod 25 that prevents the outflow ring 24 from being placed farther from the inflow ring 23 than the height of the valve 23.

Figure 11:
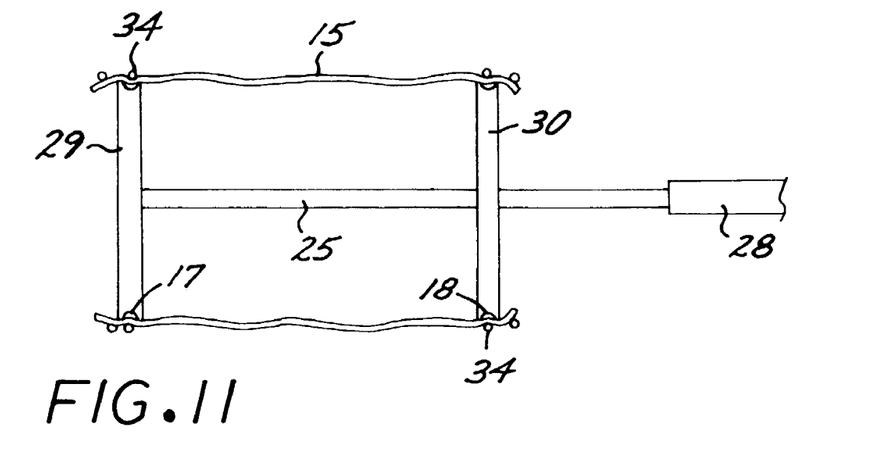
FIG. 11 is a schematic side view of the second preferred embodiment of the valve holder of the present invention.

Referring still to the second preferred embodiment of the holder of the present invention shown in FIGS. 10B, 11 and 12B, both disks 29 and 30 have circumferential grooves 33 to secure the inflow and outflow orifices of the reed valve 15 with an elastic band, suture or other fastening device known in the art. FIG. 11 shows an elastic band or suture 34 positioned in the groove 33 of the inflow disk 29 holding the valve 15 therein. The holding by the elastic band or suture 34 is reinforced by the fact that the diameter of the inflow stent 17 is slightly smaller than the diameter of the inflow disk 29. Similarly, a band or suture 34 (or several sutures) is used to support the outflow orifice of the valve 15 on the outflow disk 30 of the holder of the present invention. The diameter of the outflow stent 18 is smaller than the diameter of the inflow 29 and outflow 30 disks of the holder.

FIG. 10*b* discloses still another feature of the second preferred embodiment of the holder. Three flexible chords 35 stretch between the disks 29 and 30. The cords 35 are attached at the respective locations of the disk markers 32 corresponding to the three commissures 20 of the reed valve 15. The chords 35 are made of thin wire or plastic line (such as a polypropylene suture) and are as long as the height of the prosthetic valve 15. Also, if the valve prosthesis 15 is intended to be used as an aortic or pulmonary valve, the length of each chord 35 can be different. Our previous work on the normal anatomy of the human aortic and pulmonary valves has shown that there is a tilting angle between the planes of the inflow and outflow orifices. This tilting angle is about 11 degrees and directed posteriorly and toward the right of the patient This tilt angle corresponds to the curvature of the ascending aorta and pulmonary trunk. Therefore, the reed valve 15 of the present invention can also be constructed to tilt the plane of the outflow orifice in relation to the inflow orifice. The chords 35 of this embodiment of the valve 15 prevent overstretching of the valve even if an appropriate holder is not used in conjunction with the implantation of the valve 15.

FIG. 12B discloses that the disks 29 and 30 can be tilted on the rod 25 so that their effective diameter is reduced to allow the holder to be placed into and to be removed from the valve 15. Precise mechanisms or means for enabling these functions of temporarily reducing the effective diameter of the rings 23 and 24 in the first preferred embodiment of the holder and of the disks 29 and 30 in the second preferred embodiment so as to enable the placement and removal of the holder from the valve 15, can be constructed by those of ordinary skill in the art in light of the present disclosure. For this reason, a more detailed description here is not considered necessary.

Mounting the reed valve 15 to the holder prior to implantation involves the following steps. The inflow ring 23 or disk 29 attached to the rod 25 is pushed through the reed valve 15 until it is stopped by the inflow stent 17. A fastening suture or band 34 is positioned in the groove 33 affixing the valve 15 to the holder at that location. Then the outflow disk 30 is pulled toward the outflow orifice of the valve 15 as far as the outflow stent 18 allows. The outflow orifice of the reed valve 15 is then attached to the groove 33 of the disk 30 with a fastening suture or band 34.

Still another preferred embodiment of the holder is shown in FIG. 13. While in the previous embodiments the valve 15 was held with a holder placed within the lumen of the valve 15, this embodiment consists of a cage 36 that holds the valve 15 within the cage 36. The cage 36 comprises two rings 37 and 38 to which the inflow and outflow stents 17 and 18 of the valve 15 are fastened with sutures. The rings 37 and 38 are connected by three thin wire rods 39. The wire rods 39 are joined beyond the outflow orifice of the valve 15 and end in the handle 28.

Referring now to FIG. 14 three arms 40 made of a thin wire or flexible plastic material interconnect the inflow 17 and outflow 18 stents at the level corresponding to the commissures 20 of the tissue valve 15. The connecting arms 40 are affixed to the stents 17 and 18 by any suitable method known in the art, such as suturing. The connecting arms 40 can also be cut and removed after the reed valve 15 has been sutured into the patient. The object of the connecting arms 40 is to facilitate the correct orientation and distance between the inflow 1 and outflow orifices 2 of the tissue valve 15 after the inflow orifice 1 has been sutured in place. Twisting and over- or under-stretching of the valve 15 is therefore avoided.

In summary of the procedure applied in accordance with the present invention when the reed valve 15 of the present invention is made by the surgeon in the operating room, a reed valve (aortic, pulmonary, or venous) that comprises three leaflets is first made of autologous pericardium. The flat pericardium membrane 10 is placed on a template 9 of the appropriate size and shape. The material is trimmed to acquire the desired form. The trimmed membrane has such a shape that when its lateral aspects are joined together, a truncated cone is formed with a larger base (or inflow) orifice and a smaller, upper (or outflow) orifice. The base (or inflow) orifice is in a single plane and corresponds to the base of the new reed valve. The outflow orifice has three curvatures corresponding to the three free edges of the reed valve. The three points joining the three curvatures correspond to the three commissures of the new reed valve. The height of the membrane at the level of the three commissures corresponds to the distance between the base of a normal aortic valve and its commissures, adding a few millimeters so as to increase the area of coaptation of the new leaflets. Before the lateral sides of the membrane are sutured together, a thin wire or thick line, such as 2/0 polypropylene filament, is sutured to the base of the membrane. This suture can either be threaded through the membrane approximately 2 mm from its edge or held on to the membrane with another suture. Another similar wire or suture is also passed through the tips of the commissures of the reed valve of the present invention. After the lateral sides of the membrane have been sutured together resulting in a truncated cone, the extremities of the basal and the commissural sutures or stents are joined together either by tying them together or by one of the well-known methods in the previous art (such as crimping). In this manner, a truncated cone is formed with two supporting cables that maintain circular inflow and outflow orifices of the reed valve of the present invention. If desired, three sutures with a length that allows maximum expansion of the pericardium are passed to join the inflow and outflow stents at the level of the commissures.

The steps that follow may be performed with or without using a holder constructed in accordance with the present invention, but using the holder is advantageous because it makes it easier to perform the operation. Thus, after removal of the patient's diseased valve cusps, the base of the new valve (truncated cone including the stent) is sutured to the patient's aortic or pulmonary base with interrupted or running sutures, which per se are well known in the art. Next, the three commissural points of the truncated cone corresponding to the outflow orifice of the prosthesis are stitched to the patient's aortic wall approximately 2 to 3 mm beyond the patient's own commissures. If the surgeon decides to have a completely stentless prosthesis, both stents and, if present in the valve, three connecting arms are cut and removed. If the surgeon decides to retain the outflow stent, a running, small-caliber suture is used to anchor the outflow stent to the sinotubular junction of the patient. The inflow stent is designed to maintain the circular geometry of the inflow orifice of the reed valve, and the outflow stent is designed to ensure that the three commissures of the reed valve are equidistant. This is particularly important in cases where the distance between the patient's commissures is variable.

The decision to retain the two supporting stents depends on the pathology encountered by the surgeon. In some patients, the base of the aortic valve is abnormally dilated. In others, the sinotubular junction is abnormally dilated. Further, both the base and the sinotubular junction can be dilated. To avoid progressive dilatation, these cases require the presence of the support offered by the inflow and outflow stents.

What is claimed is:

1. A process of surgically implanting an intravascular one-way valve having a plurality of leaflets, to serve as a prosthesis for a diseased native valve of a mammal, into the blood vessel of a mammal in need of such implantation,
   the process comprising the steps of:
   suturing the inflow orifice of the valve into a base in a blood vessel of the mammal, and
   suturing the outflow orifice to the mammal's blood vessel only at the comissures, the valve comprising:
   a tubular member formed of one of a naturally occurring tubular body channel and of a membrane, the membrane being selected from a group of materials consisting of biocompatible polymer and biologic flat membrane, said membrane configured as a truncated cone, the tubular member having an inflow orifice and an outflow orifice, the leaflets forming the outflow orifice and forming a plurality of commissures;
   a first flexible stent consisting essentially of material selected from the group consisting of thin metal wire, thin plastic ring, or suture filament, said first stent being removably affixed in a substantially circular fashion around the tubular member in proximity of the inflow orifice, and
   a second flexible stent consisting essentially of material selected from the group consisting of thin metal wire, thin plastic ring, or suture filament, said second stent being removably affixed at the location of the commissures to form a circle around the tubular member in proximity of the outflow orifice the valve.

2. A process in accordance with claim 1 additionally comprising the step of severing the first stent and removing it from the valve being implanted.

3. A process in accordance with claim 1 additionally comprising the step of severing the second stent and removing it from the valve being implanted.

4. A process in accordance with claim 1 additionally comprising the steps of severing the first and second stents and removing them from the valve being implanted.

* * * * *